United States Patent [19]

Michaelis et al.

[11] Patent Number: 5,561,110
[45] Date of Patent: Oct. 1, 1996

[54] METHOD FOR THE TREATMENT OF THE COMPLICATIONS AND PATHOLOGY OF DIABETES

[75] Inventors: Jurgen Michaelis, Kariong, Australia; Alan R. Hipkiss, St Albans, United Kingdom; Sianna Panagiotopoulos, Doncaster, Australia

[73] Assignees: Peptide Technology Limited, New South Wales, Australia; King's College London, London, England

[21] Appl. No.: 204,242

[22] PCT Filed: Sep. 9, 1992

[86] PCT No.: PCT/AU92/00480

§ 371 Date: Jul. 27, 1994

§ 102(e) Date: Jul. 27, 1994

[87] PCT Pub. No.: WO93/04690

PCT Pub. Date: Mar. 18, 1993

[51] Int. Cl.$^6$ .................................................. A61K 38/16
[52] U.S. Cl. ................................. 514/13; 514/4; 514/14
[58] Field of Search ................................ 514/13, 14, 4

[56] References Cited

U.S. PATENT DOCUMENTS

| | | | |
|---|---|---|---|
| 4,508,728 | 4/1985 | Nagai et al. | 514/400 |
| 4,717,716 | 1/1988 | Nagai et al. | 514/49 |

FOREIGN PATENT DOCUMENTS

| | | |
|---|---|---|
| 0303380 | 2/1989 | European Pat. Off. . |
| 0313654 | 5/1989 | European Pat. Off. . |
| WO90/06102 | 9/1989 | WIPO . |

OTHER PUBLICATIONS

Merck Manual Fifteenth Edition, Merck & Co., Rahway, NJ (1987). see pp. 1120–1121.

*Primary Examiner*—Christine M. Nucker
*Assistant Examiner*—Jeffrey Stucker
*Attorney, Agent, or Firm*—Nixon & Vanderhye

[57] ABSTRACT

The present invention provides a method for the treatment of the complications and pathology of diabetes. The method involves the administration to a diabetic subject of a composition comprising a compound selected from the group consisting of ($\beta$-Ala-His)$_n$, (Lys-His)$_n$, a compound of the formula $R_1$-X-$R_2$, pharmaceutically acceptable salts thereof and combinations thereof; and a pharmaceutically acceptable carrier, in which n is 2-5, $R_1$ is one or two naturally occurring amino acids, optionally alpha-amino acetylated with alkyl or aralkyl of 1 to 12 carbon atoms, preferably 2 to 6 carbon atoms, $R_2$ is 1 or 2 naturally occurring amino acids, optionally alpha-carboxyl esterified or amidated with alkyl or aralkyl of 1 to 12 carbon atoms, preferably 2 to 6 carbon atoms and X is $R_3$-L or D-His ($R_4$)-$R_5$ where $R_3$ is void or $\omega$-aminoacyl with 1 to 12 carbon atoms, preferably 2 to 6 carbon atoms, $R_4$ is void or imidazole modification with alkyl-sulphydryl, hydroxyl, halogen and/or amino groups, and $R_5$ is void or carbonyl (alkyl) amides with 1 to 12 carbon atoms, preferably 2 to 6 carbon atoms. Preferably, the compound is carnosine.

16 Claims, 2 Drawing Sheets

FIG. 1
REACTION OF CARNOSINE WITH SUGARS

FIG. 2
ARTHEROSCLEROSIS

FIG. 3

METHOD FOR THE TREATMENT OF THE COMPLICATIONS AND PATHOLOGY OF DIABETES

The present invention relates to a method of treating the complications and pathology of diabetes.

The di-peptide carnosine, was discovered about 90 years ago (Gulewitsch and Amiradzibi, 1900) as a heat-stable extract derived from meat; since these early origins, considerable data has accumulated on the distribution and metabolism of the di-peptide. Carnosine (β-alanyl-L-histidine) and its related compounds such as anserine (β-alanyl-1-methyl-L-histidine) and homocarnosine (γ-amino-butyryl-L-histidine) are present in millimolar concentrations in numerous mammalian tissues, including skeletal muscle (2–20 mM) and brain (0.3–5 mM). Although no unified hypothesis exists to account for physiological function of this group of di-peptides, their antioxidant properties, ability to protect DNA from radiation damage, ability to chelate divalent cations, and remarkable buffer capacity at physiological pH-values has led to the proposal that their primary function in vivo is to furnish protection to proteins, lipids and other macromolecules.

In addition to its role as free radical scavenger carnosine has been claimed to act as an "immunoregulator" (Nagai, Patent: GB 2143732A) with useful properties in the treatment of certain cancers (Nagai, Patent DE 3424781 A1). Carnosine has also been suggested to be useful in the treatment of lipid peroxide induced cataracts (Babizhayev, 1989). There is also evidence that carnosine can accelerate the process of wound healing.

Non-enzymatic Glycosylation

Free-radical damage is not the only process to affect the structure of proteins and nucleic acids. Non-enzymatic glycosylation (glycation), the Maillard reaction in food chemistry (Maillard, 1912, or browning reaction, involves reaction of amino groups with sugar aldehyde or keto groups to produce modified amino groups and eventually forming advanced-glycosylation-end-products (AGE-products). Although glycation is slow in vivo, it is of fundamental importance in ageing and in pathological conditions where sugar levels are elevated, e.g. diabetes.

It is possible to demonstrate glycation of proteins in the test tube. Several studies have shown that most proteins and DNA are potential targets for non-enzymic glycosylation in which sugars become attached to amino groups in the molecule via a Schiff's base. Subsequently a rearrangement occurs to give the coloured product (called the Amadori product). Further slow and uncharacterised reactions of the Amadori products occur.

Analysis of the preferred glycation sites in proteins shows the epsilon amino groups of lysine residues are primary targets, particularly when in proximity to histidine residues (Shilton & Walton, 1991). In a search for stable peptides with long half-lives in vivo we found that the amino acid sequence of carnosine is similar to Lys-His, thus having the potential to react with sugars and react as scavenger for aldehyde groups. In addition carnosine is virtually non-toxic; well documented toxicity studies have indicated that the material can be administered to mammals to a level of 5–10 g/kg body weight and therefore no toxic side effects are expected over long-term treatment.

So far only one other compound has been shown to slow down glycation by reacting with sugars and blocking the Amadori re-arrangement. Aminoguanidine can reduce both in vitro and in vivo glucose-derived advanced glycation end products. Unfortunately aminoguanidine, a nucleophilic hydrazine compound, is nonphysiological and is of unknown long-term toxicity.

Diabetes

Diabetes is a metabolic disorder caused by an acute or chronic deficiency of insulin. It is diagnosed by an increased blood glucose level. The acute condition is characterised by a reduced glucose uptake of the insulin-dependent tissues. The body counteracts the resulting energy deficiency by increasing lipolysis and reducing glycogen synthesis. When the diabetic condition is severe, calories are lost from two major sources; glucose is lost in the urine, and body protein is also depleted. This is because insufficiency of insulin enhances gluconeogenesis from amino acids derived from muscle. The acute disorder can be controlled by insulin injections but since the control can never be perfect, the long-term fate of a diabetic is dependent on complications occurring later in life in the eye (cataractogenesis and retinopathy), kidney (nephropathy), neurons (neuropathy) and blood vessels (angiopathy and artherosclerosis). It is well established that coronary heart disease is one of the most common causes of deaths in diabetics and non-diabetics alike.

Analyses of urine protein are usually requested in diabetic patients to rule out the presence of serious renal disease (nephropathy). A positive urine protein result may be a transient or insignificant laboratory finding, or it may be the initial indication of renal injury. The most serious proteinuria is associated with the nephrotic syndrome, hypertension, and progressive renal failure. In these conditions, the glomeruli become increasingly permeable to proteins by mechanisms that are poorly understood. The consequences are extremely serious, since they can progress rather rapidly to total renal failure and ultimate death. This form of proteinuria occurs as a secondary consequence to diseases like diabetes, amyloidosis and lupus erythematosus.

As in other complications of diabetes, consideration of a potential role for glycation in the development of retinopathy must be taken into account. The retinal capillaries contain endothelial cells which line the capillary lumen and form a permeability (blood-retinal) barrier, and pericytes (mural cells), which are enveloped by basement membrane produced by the two cell types. Intramural pericytes are selectively lost early in the course of diabetic retinopathy, leaving a ghost-like pouch surrounding basement membrane. Breakdown of the blood-retinal barrier is another failure. Aldose reductase inhibitors are under investigation in treatment of experimental retinopathy in animals. Their mechanism of action is the prevention of the accumulation of sorbitol and resulting osmotic changes. However, the link with non-enzymatic glycosylation becomes obvious by the fact that Hammes et al (1991) have shown that treatment with aminoguanidine inhibits the development of experimental diabetic retinopathy. It is very likely that other potential inhibitors of glycation like carnosine should also have a positive effect.

Glycation and Atherosclerosis

Recent studies have suggested that AGE may have a role in the development of atherosclerosis. This is based on the finding that human monocytes have AGE specific receptors on their surface and respond when stimulated by releasing cytokines. Minor injury to the blood vessel wall may expose sub-endothelial AGE and promoting the infiltration of monocytes and initiating the development of atherosclerotic lesion. Circulating lipoproteins can also undergo glycation which is then taken up by endothelial cells at a faster rate than non-glycated lipoprotein. This is of importance in diabetes where an increased serum level of glycated lipoproteins has been reported. A compound with anti-glycation properties like carnosine should therefore have a positive effect on vascular diseases.

The reason for the diabetic complications are not fully understood as a continuous release of insulin after subcutaneous injections may not be adequate to respond to varying glucose concentrations necessary to avoid periodic hyperglycaemic conditions. Therefore, blood sugar levels in diabetics can be on average higher than in normal individuals resulting in an increased level of glycation. The best example are glycohaemoglobins which form non-enzymatically in red blood cells in amounts proportional to the cellular glucose levels. The higher percentage of glycated haemoglobin and serum albumin is used to monitor the degree of a diabetic's hyperglycaemia.

A controlled dietary intake of compounds which can counteract the long-term effects of high glucose levels in blood would be beneficial as an addition to a controlled diabetes therapies, such as insulin administration, sulfonylurea and biguanide treatment, on the use of amylin blockers. It is only the open chain form of reducing sugars like glucose, galactose, fructose, ribose and deoxyribose which participate in glycation. By scavenging this free aldehyde group and binding it in a non-toxic form we believe that it should be possible to decrease the damage caused by high sugar levels in vivo and in vitro. The compounds which are proposed for the treatment of the complications and pathology of diabetes could be peptides with one or more of the following characteristics:

1) they should be non-toxic even at relatively high doses;

2) they should be resistant to cleavage by non-specific proteases in the intestine and be taken up intact into the blood and organs, but should be cleared by kidneys, thereby following a similar tissue distribution to glucose in diabetes;

3) the peptides should react rapidly with reducing sugars compared with amino groups on protein surfaces;

4) the resultant glycated peptides should not be mutagenic, in contrast to glycated amino acids, 5) if the peptide is cleaved by specific proteases in blood and tissue the resulting amino acids should be of nutritional value for diabetics, for example facilitating gluconeogenesis and counteracting a negative nitrogen balance.

SUMMARY OF THE INVENTION

The present inventors believe that peptides having similar activity to that of canosine may be useful in the treatment of the complications and pathology of diabetes.

Accordingly, in a first aspect the present invention consists in a method for the treatment of the complications and pathology of diabetes in a diabetic subject comprising administering to the subject a composition comprising a compound selected from the group consisting of ($\beta$-Ala-His)$_n$, (Lys-His)$_n$, a compound of the formula $R_1$-X-$R_2$, pharmaceutically acceptable salts thereof and combinations thereof; and a pharmaceutically acceptable carrier, in which n is 2-5, $R_1$ is one or two naturally occurring amino acids, optionally alpha-amino acetylated with alkyl or aralkyl of 1 to 12 carbon atoms, preferably 2 to 6 carbon atoms, $R_2$ is 1 or 2 naturally occurring amino acids, optionally alpha-carboxyl esterified or amidated with alkyl or aralkyl of 1 to 12 carbon atoms, preferably 2 to 6 carbon atoms and X is $R_3$-L or D-His ($R_4$)-$R_5$ where $R_3$ is void or $\omega$-aminoacyl with 1 to 12 carbon atoms, preferably 2 to 6 carbon atoms, $R_4$ is void or imidazole modification with alkyl-sulphydryl, hydroxyl, halogen and/or amino groups, and $R_5$ is void or carbonxyl (alkyl) amides with 1 to 12 carbon atoms, preferably 2 to 6 carbon atoms.

In a second aspect the present invention consists in the use of a compound selected from the group consisting of ($\beta$-Ala-His)$_n$, (Lys-His)$_n$, a compound of the formula $R_1$-X-$R_2$, pharmaceutically acceptable salts thereof and combinations thereof; in which n is 2-5, $R_1$ is one or two naturally occurring amino acids, optionally alpha-amino acetylated with alkyl or aralkyl of 1 to 12 carbon atoms, preferably 2 to 6 carbon atoms, $R_2$ is 1 or 2 naturally occurring amino acids, optionally alpha-carboxyl esterified or amidated with alkyl or aralkyl of 1 to 12 carbon atoms, preferably 2 to 6 carbon atoms and X is $R_3$-L or D-His ($R_4$)-$R_5$ where $R_3$ is void or $\omega$-aminoacyl with 1 to 12 carbon atoms, preferably 2 to 6 carbon atoms, $R_4$ is void or imidazole modification with alkyl-sulphydryl, hydroxyl, halogen and/or amino groups, and $R_5$ is void or carbonxyl (alkyl) amides with 1 to 12 carbon atoms, preferably 2 to 6 carbon atoms, in the preparation of amedicament for the treatment of the complications and pathology of diabetes.

In a preferred embodiment of the present invention $R_1$ and $R_2$ are L- or D-lysine or L- or D-aspartic acid or L- or D-glutamic acid or homologues thereof. In a preferred form of the invention the compound is selected from the group consisting of carnosine, anserine, ophidine, homocarnosine, homoanserine, D-carnosine, and carcinine, it is presently most preferred that the compound is carnosine.

In a further preferred embodiment of the present invention the composition may include other compounds which have a beneficial effect in the treatment of the complications and pathology of diabetes, such as aminoguanidine.

Further, as a number of the subjects to be treated may also be on insulin sulfonylurea, biguanide or amylin blocker therapy the composition of the present invention may be co-administered with the insulin sulponyurea, biguanide or amylin blockers therapy.

Further information regarding sulponylurea acid biguanide therapy can be found in Beck-Nielsen "Pharmacology of Diabetes", Eds. C. E. Mogensen and E. Standl, 1991, pp 75–92, the disclosure of which is incorporated by reference.

Further information on the use of amylin blocker therapy in diabetes can be found in Westermerk et al 1987 DNAS 84, 3881–3885, the disclosure of which is incorporated herein by reference.

One of the major drawbacks with insulin therapy is the continued need for injections. The present invention may provide an alternative in the oral administration of carnosine with biguanides or sulfonylureas which may be more attractive to diabetics.

The composition of the present invention may be administered in any suitable manner such as injection, infusion, ingestion, inhalation, iontophoresis or topical application. It is presently preferred, however, that the composition is administered orally.

In yet a further preferred embodiment the active compound is mixed with or linked to another molecule which molecule is such that the composition is improved in regard to skin penetration, skin application, tissue absorption/adsorption, skin sensitisation and/or skin irritation. The molecule is preferably selected from the group consisting of sodium lauryl sulphate, lauryl ammonium oxide, ozone, decylmethylsulphoxide, lauryl ethoxylate, octenol, dimethylsulphoxide, propyleneglycol, nitroglycerine, ethanol and combinations thereof.

It is also possible that the compound may be in the form of a prodrug. Further information on prodrug technology can be found in "A Text Book of Drug Design and Development", edited by Povl Krogsgaard-Larsen and Hans Bundgaard, Chapter 5 "Design and Application of Prodrugs", H. Bundgaard. The disclosure of this reference is incorporated herein by cross-reference.

As stated above it is preferred that the composition of the present invention is administered orally. As will be understood by those skilled in the art numerous modifications can be made to the composition to improve the suitability of the composition for oral delivery. Further information on oral delivery can be found in "Peptide and Protein Drug Delivery" edited by Vincent H. L. Lee, Chapter 16 "Oral Route of Peptide and Protein Drug Delivery", V. H. L. Lee et al. The disclosure of this reference incorporated herein by cross-reference.

As stated above the composition may be administered by injection. Injectable preparations, for example, sterile injectable aqueous, or oleagenous suspensions may be formulated according to methods well known to those skilled in the art using suitable dispersion or wetting agents and suspending agents. The sterile injectable preparation may also be a sterile injectable solution or suspension in a non-toxic parenterally acceptable diluent or solvent. Among the acceptable vehicles and solvents which may be employed are water, Ringer's solution, and isotonic sodium chloride solution. In addition, sterile, fixed oils are conventionally employed as a solvent or suspending medium. For this purpose, any bland, fixed oil may be employed including synthetic mono- or diglycerides. In addition, fatty acids, such as oleic acid find use in the preparation of injectables.

The total daily dose of the composition to be administered will depend on the host to be treated and the particular mode of administration. It will be understood that the specific dose level for any particular patient will depend on variety of factors including the activity of the specific compound employed, the age, bodyweight, general health, sex, diet, time of administration, route of administration, rate of excretion, and the severity of the particular side effects undergoing therapy. It is believed that the selection of the required dose level is well within the expertise of those skilled in this field.

It is believed that the dosage for carnosine would be in the range of 20 mg to 2 g/kg body weight/day and preferably in the range of 100 mg to 200 mg/kg bodyweight/day.

As stated above one of the complications associated with diabetes is cataracts. Accordingly, one particularly preferred mode of administration of the composition of the present invention is opthalmic administration. In this situation the pharmaceutically acceptable carrier will be sterile aqueous or non-aqueous solutions, suspensions, emulsions and ointments. Examples of suitable pharmaceutically acceptable vehicles for opthalmic administration are proplyene glycol, and other pharmaceutically acceptable alcohols, sesame or peanut oil and other pharmaceutically acceptable oils, petroleum jelly, water soluble opthalmically acceptable non-toxic polymers such as methyl cellulose, carboxymethyl cellulose salts, hydroxy ethyl cellulose, hydroxy propyl cellulose; acrylates such as polyacrylic acid salts, ethylacrylates, polyacrylamides, natural products such as gelatine, alginates, pectins, starch derivatives such as starch acetate, hydroxy ethyl starch ethers, hydroxy propyl starch as well as other synthetic derivatives such as polyvinyl alcohol, polyvinyl pyrolidone, polyvinyl methylether, polyethylene oxide, carbopol and xantham gum and mixtures of these polymers. Such compositions may also contain adjuvants such as buffering, preserving, wetting, emulsifying dispersing agents. Suitable preserving agents include antibacterial agents such as quartenary ammonium compounds, phenylImercuric salts, benzoyl alcohol, phenyl ethanol, and antioxidants such as sodium metabisulphide. Suitable buffering agents include borate, acetate, glyconate and phosphate buffers. The pharmaceutically opthalmic compositions may also be in the form of a solid insert.

As will be clear from the foregoing discussion the complications and pathology of diabetes are treated by reducing or preventing non-enzymatic glycosylation. Accordingly, it could be expected that the method of the present invention would also be useful in the treatment of other adverse complications and pathology of other disease states which are due to non-enzymatic glycosylation.

In order that the nature of the present invention may be more clearly understood, preferred forms thereof will now be described with reference to the following examples and figures in which.

DETAILED DESCRIPTION OF THE INVENTION

Methods:

Reaction of Peptides and Amino Acid Derivatives with Sugars

Unless otherwise stated, reactions were carried out in phosphate buffered saline, PBS, (140 mM-NaCl/10 mM-sodium phosphate, pH 7.4) in sealed microcentrifugation vials in a 60° C. waterbath. The reaction mixture contained 50 mM peptide and 500 mM sugar. At specified time points samples were taken, diluted 1:20 with water, and stored at −20° C. prior to analysis by HPLC.

Detection of Amino Groups

For the detection of free amino groups on peptides the Waters AUTO. OPA™ was used (Waters AUTO.TAG™ operation manual). In brief, peptides were reacted with o-phthalaldehyde and the fluorescent derivative separated by HPLC on a Radical-PAK™ $C_{18}$ column using a 10% (v/v) to 90% (v/v) methanol gradient over 15 min as solvent. A Waters 470 fluorescence detector set at excitation 340 nm/emission 440 nm was used.

Gelfiltration Chromatography of Glycated Proteins
HPLC Specifications:

COLUMN Superose 6, Pharmacia

SAMPLE: 100μ of Protein Sample (Approximately 100 μg)

ELUENT: 10 mM phosphate buffer pH 7.38, 140 mM NaCl, 2 mM KCl, 0.02% $NAN_3$, 0.05% Tween 20

FLOR RATE: 0.5 ml/min

DETECTION: 280 nm.

Calibration was performed using Pharmacia high molecular weight (HMW) and low molecular weight (LMW) calibration kit.

| CALI-BRA-TOR | COMPONENTS | MOLECULAR WEIGHT | RETEN-TION TIMES | |
|---|---|---|---|---|
| HMW | Blue Dextran | >2,000,000 | 15.49 | n = 5 |
| | Thyroglobulin | 669,000 | 25.84 | n = 6 |
| | Ferritin | 440,000 | 29.73 | n = 5 |
| | Catalase | 232,000 | 32.58 | n = 6 |
| | Aldolase | 158,000 | 32.58 | n = 6 |
| | | | Co-elute | |
| LMW | Blue Dextran | >2,000,000 | 15.65 | n = 5 |
| | Albumin | 67,000 | 33.74 | n = 6 |
| | Ovalbumin | 43,000 | 35.57 | n = 5 |
| | Chymotrypsin A | 25,000 | 39.23 | n = 6 |
| | Ribonuclease A | 13,700 | 39.23 | n = 6 |
| | | | Co-elute | |

Analysis of mutagenic potential of glycated compounds, "Ames Test"

Preparation of glycated compounds was performed according to Kim et al. (1991). In brief, D-glucose (1M) and each of the following: L-carnosine, L-lysine, L-alanine (all 1M) were dissolved in distilled water, the pH adjusted to 7 and the mixtures heated at 100° C. for 80 min. The solutions (50 μl and 250 μl) were evaluated against strain TA 100 of *Salmonells typhimurium* using the plate incorporation method (Maron & Ames, 1983) with or without metabolic activation by a standard rat liver microsomal (S-9) preparation. 2-AF and 2-AAF were used as positive controls for the experiments with metabolic stimulation, otherwise sodium azide was included as strain specific positive control.

The Effect of Carnosine on Atherosclerosis

Male New Zealand white cross rabbits fed a high cholesterol (2%) diet were randomised to control or carnosine treatment 2% and plasma was assayed for cholesterol and triglycerides and carnosine. All animals received 100 g of food pellets/day and free access to water.

At the end of the 8 week treatment period, the rabbits were anaesthetised with pentobarbitone (325 mg/kg) and the total aorta removed. The arch, thoracic and abdominal regions were isolated by cutting the aorta circumferentially 1.0 cm proximal to the first pair of intercostal arteries and 0.3 cm above the coeliac artery. The adventitia was carefully dissected away, and the artery longitudinally cut to expose the intimal surface. The aorta was fixed in 10% buffered formalin for 48 hours. The lipid plaques in these vessels were then stained using Sudan IV and mounted with an aqueous mounting medium (Kaiser's Glycerol Jelly). The lesioned areas were directly traced from the mounted sections using an image analyser (Eye Com 850 image processor). Computer-aided planimetry was used to macroscopically determine the percentage of the affected area. Representative segments of atherosclerotic plaque were removed for confirmation by light microscopy. Results are expressed as mean ±SEM.

Formation of Cataracts in Diabetic Rats

Male Sprague-Dawley rats weighing 200–250 g and 6 weeks of age were randomised to the following three treatment groups: control, diabetic, and carnosine-treated diabetic rats. Diabetes was induced with streptozotozen STZ(60 mg/kg body weight in citrate buffer, pH 4.5, i.v.), and all animals with plasma glucose levels > 20 mM after 1 week were included in the study. Diabetic rats were randomised to receive either no therapy or 2% carnosine in drinking water.

Results

EXAMPLE 1

Reaction of Carnosine with Sugar

The rate of reaction between aldehydes and amino groups in glycation is dependent solely on temperature and reactant concentration, thus allowing the use of non-physiological conditions in in vitro experiments to speed up the reaction without affecting the equilibrium. The first step in the Maillard reaction, the formation of a Schiff base between aldehyde and primary amino group, varies according to amount of linear chain form of the sugar. This is followed by an Amadori rearrangement and complicated secondary reactions, most of which are poorly understood.

Figure 1:
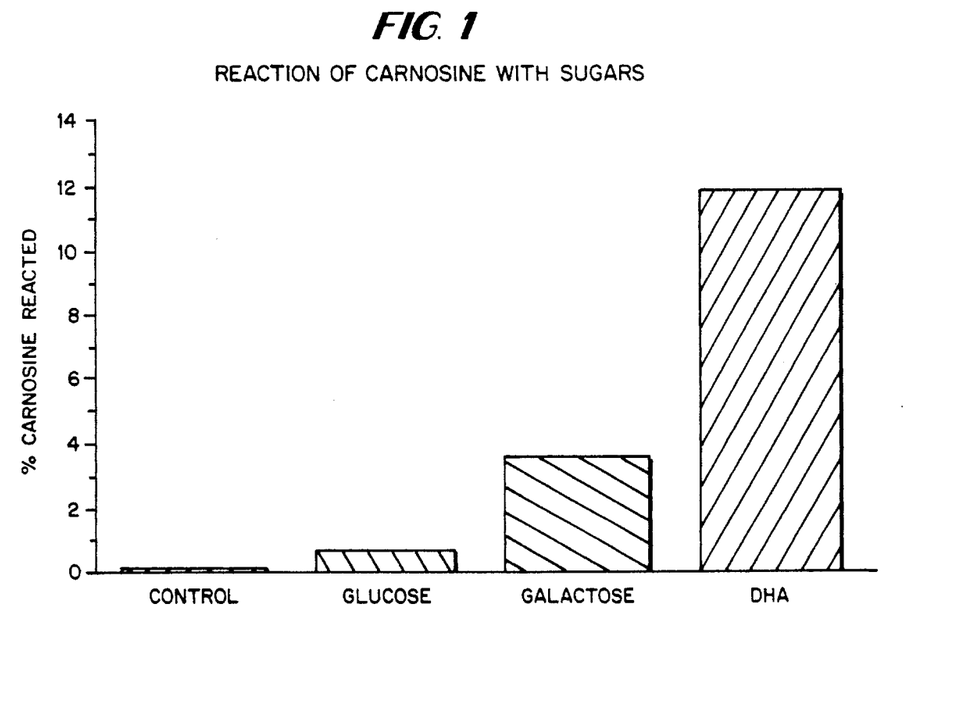
FIG. 1 shows the reaction rate of L-carnosine with sugars. L-carnosine (60 mM) was reacted with sugars (180 mM) in 50 mM na-phosphate buffer pH7 for five hours at 60° and the loss of the free amino group of carnosine assayed by HPLC. SEM < ±1% of total carnosine in incubation mixture.

Incubation of glucose, galactose and dihydroxyactetone (DHA) with carnosine produced brown solutions characteristic of glycation as originally described by Maillard (1912). The reaction of carnosine with the sugars was followed by disappearance of free amino group measured flurometrically after HPLC. Glucose, galactose and DHA differed in their reaction with carnosine (FIG. 1). Glucose was the least reactive and DHA the most, showing at least a fifteen-fold difference. For convenience we chose to employ the triose DHA in most subsequent studies.

EXAMPLE 2

Prevention of dihydroxyacetone induced modification of bovine serum albumin by carnosine Physiological concentrations of bovine serum albumin (50 mg/ml in 50 mM Na-phosphate buffer pH 7.0) were incubated with or without 250 mM dihydroxyacetone in the presence and absence of 250 mM L-carnosine at 23° C. for 4 weeks. The experiment was performed under sterile conditions and the ionic strength was the same in all vials. The results are shown in table 1.

In this long-term experiment dihyroxyacetone had glycated albumin and, as a result of an Amadori rearrangement, subsequently induced the formation of a solid gel. When carnosine was present the contents of the vial remained fluid.

TABLE 1

| Incubation conditions | Resultant effects |
|---|---|
| Albumin + phosphate buffer | colourless, fluid. |
| Albumin + dihydroxyacetone | brown, firm gel. |
| Albumin + dihydroxyacetone | dark brown, fluid. |

The effects of carnosine on dihydroxyacetone-induced non-enzymic glycosylation of bovine serum albumin.

EXAMPLE 3

Comparison of the reaction rate of carnosine and different amino acids with glucose Slow non-enzymic glycosylation of proteins and nucleic acids by glucose can be accelerated in vitro by raising the temperature from physiological values to 50° C. The main targets of glucose in vivo and in vitro are basic amino acids lysine and arginine (either free or following their incorporation into proteins). Table 2 shows a comparison of the reaction of carnosine and different amino acids with glucose. In order to demonstrate the specificity of the Maillard reaction for reducing sugars, glucose was substituted by sorbitol (a non-reducing sugar). 500 μl of glucose or sorbitol (250 mg/ml in 50 mM Na-phosphate buffer pH 7.0) were incubated with different amino acids or carnosine (500 mM) at 50° C. for 18 h. The optical densities at 400 nm of the resultant solutions were measured (Table 2). Carnosine formed by far the most Maillard reaction product, approximately 2-times or 8-times more than the fastest reacting amino acid, L-lysine or beta-alanine respectively. A small amount of Maillard reaction product is also apparent when carnosine reacts with sorbitol, probably due to autoxidation of sorbitol to a reducing sugar.

TABLE 2

Optical density at 400 mm of Maillard reaction products between dipeptides or amino acids with glucose or sorbitol

| Incubation conditions | OD 400 nm |
|---|---|
| glucose + PBS | 0.175 |
| glucose + carnosine | 8.455 |
| sorbitol + PBs | 0.000 |
| sorbitol + carnosine | 0.209 |
| carnosine + PBS | 0.041 |
| glucose + D, L-alanine | 0.266 |
| sorbitol + D, L-alanine | 0.008 |
| glucose + beta-alanine | 1.240 |
| sorbitol + beta-alanine | 0.010 |
| glucose + L-arginine | 0.469 |
| sorbital + L-arginine | 0.010 |
| glucose + L-lysine | 170 |
| sorbitol + L-lysine | 0.009 |
| glucose + imidazole | 0.046 |
| sorbitol imidazole | 0.035 |

EXAMPLE 4

Reaction of carnosine, related peptides and amino acids with dhydroxyacetone When the reaction rates of carnosine, related peptides and amino acids with DHA were compared (Table 3), carnosine reacted faster than lysine, which suggested that the dipeptide could compete against other sources of amino groups for glycation. However, in this assay lysine had two amino groups contributing to its reactivity whereas in proteins only the epsilon amino group is usually available. To compare the glycation rate solely of the epsilon amino group, N-alpha-carbobenzox-yl-lysine (Z-lysine) which as a blocked alpha amino group, was used. When DHA was added to an equimolar mixture of carnosine of Z-lysine the dipeptide reacted about ten times faster than the blocked amino acid (Table 3). The relative reactivity was retained when glucose was employed as the glycating sugar, although the experiment took ten days to complete(not shown). Ac-Lys-NHMe, a molecule which closely resembles a lysine residue incorporated into proteins, also showed a slower reaction with DHA compared to carnosine. The peptide Ac-Lys-His-NH$_2$ resembles the preferential glycation site in proteins and showed the same reactivity as does carnosine. The peptide beta-alanyl-glycine was virtually unreactive with DHA, confirming the requirement for histidine at position two in a peptide for fast glycation (Shilton & Walton, 1991). While D-carnosine (beta-alanyl-D-histidine) reacted as fast as the naturally-occurring isomer, the higher homologue, homocarnosine (gamma-amino-butyryl-L-histidine), reacted slower. This indicates that a minor structural change to carnosine (the addition of a methylene group) reduces its reactivity. It also becomes evident that modification of lysine by various groups has a significant effect on the reaction rate. Whereas Ac-Lys-NH$_2$Me (blocked amino and carboxyl group) reacted faster, Z-lysine reacted slower than the free amino acid.

It was also found that the addition of free imidazole and succinyl histidine (alpha-amino group blocked) promoted the reactivity of carnosine with DHA as shown by an increase in the rate of disappearance of the dipeptide's amino group. This is in agreement with the suggestions that imidazole either catalyses the Amadori rearrangement or reacts with an intermediate form thereby changing the equilibrium of the reaction towards AGE-products (Shilton & Walton, 1991).

TABLE 3

| | Compound | % reacted |
|---|---|---|
| A | Beta-Ala-l-His-OH | 26 |
| | Beta-Ala-D-His-OH | 26 |
| | Ac-Lys-His-NH$_2$ | 25 |
| | AC-Lys-NH$_2$Me | 21 |
| | H-Lys-OH | 17 |
| | Gamma-aminobutyryl-His-OH | 15 |
| | Z-Lys-OH | 3 |
| | Beta-Ala-Gly-OH | 2 |
| B | Beta-Ala-L-His-OH + succinyl-His | 33 |
| | Beta-Ala-L-His-OH + imidazole | 43 |

Glycation of Peptides and Amino Analogues by DHA.

A and B: Compounds were reacted with DHA in PBS for 5 hours at 60° C. and the loss of free amino group assayed by HPLC. Data are expressed as percent of amino groups reacted with DHA (SEM±1% of total peptide or amino acid in incubation mixture). B only: Succinyl-His and imidazole were added at equimolar concentrations to beta-Ala-L-His-OH and the amino group of the latter assayed.

EXAMPLE 5

Mutagenic properties of glycated amino acids and glycated carnosine

Glycated amino acids such as lysine and arginine have been reported to be mutagenic (Kim et al., 1991) in an assay system first described by Maron & Ames (1983) "Ames Test". Other glycated amino acids like proline and cysteine did not exhibit mutagenicity. We have investigated the mutagenicity of L-carnosine and the glycated froms of L-carnosine, L-lysine and L-alanine (Table 4). All four solutions appear to inhibit the indicator strain to some extent, especially at the 250 μl dose. Our data confirm earlier results by Kim et al., (1991) that glycated L-lysine is mutagenic and may therefore be carcinogenic. The activity is slightly enhanced by the rat liver S-9 metabolic activation system. Glycated L-alanine showed no mutagenicity in our experiments and only weak mutagenicity in the earlier work. Both, free carnosine and glycated carnosine are not mutagenic. This would be anticipated should carnosine play a significant role in the Maillard reaction in vivo. The reason for the difference of the glycated forms of L-carnosine and L-lysine is not known.

TABLE 4

|  |  | Revertants per Plate with TA 100 | |
| --- | --- | --- | --- |
| Compound | Dose (μl) | Without S-9 | With S-9 |
| L-carnosine | 250 | 158 ± 11 | 149 ± 13 |
|  | 50 | 154 ± 14 | 179 ± 15 |
| L-carnosine | 250 | 142 ± 17 | 158 ± 19 |
| glycated | 50 | 159 ± 7 | 167 ± 10 |
| L-lysine | 250 | 277 ± 21 | 244 ± 13 |
| glycated | 50 | 357 ± 17 | 553 ± 19 |
| L-alanine | 250 | 145 ± 6 | 146 ± 9 |
| glycated | 50 | 160 ± 9 | 181 ± 10 |
| negative control |  | 161 ± 6 | 188 ± 10 |
| + azide |  | >1000 | N/A |
| + 2AF |  | N/A | 250 ± 33 |
| + 2AAF |  | N/A | 500 |

Mutagenic potential of glycated compounds

*Salmonella tyrphimurium* TA 100 indicator strain his⁻ to his⁺ reversion system. Data represent the mean number of revertants per plate and their standard deviation for the test solutions and controls with and without metabolic stimulation by rat liver microsomal (S-9) preparation.

EXAMPLE 6

Comparison of Carnosine with Aminoguanidine as Inhibitors for Non-enzymatic glycosylation To compare the effect of both carnosine and aminoguanidine on glycation bovine serum albumin (BSA) and ovalbumin was incubated with a constant amount of DHA and varying concentrations of either anti-glycator at 60° C. At the start of the reaction and after seven hours aliquots were taken and the progress of the reaction analysed by gel filtration on a Superose 6 column. Crosslinking or fragmentation of protein became clearly visible as a change in retention time compared to the untreated protein used as control. Some compounds eluted after theoretical retention time for the smallest compound. They tend to interfere with the column resin even at high ionic strength and presence of a detergent (Tween 20). They are not necessary small compounds but rather highly charged and reactive. Table 5 summarises the data. Both compounds seem to react differently in this system: Carnosine reduced formation of high molecular weight compounds and was slightly more effective at low concentration compared to aminoguanidine. In all aminoguanidine samples uncharacterised reaction products are formed predominantly at high concentrations (described as low molecular weight form "LMW" because the retention time is longer then observed for all other compounds). Since the albumin monomer peak area is also reduced it is most likely that these are reaction products between ovalbumin, aminoguanidine and DHA. All three compounds showed no change in retention time or peak area when incubated separately under the same conditions for seven hours. LMW were also observed when ovalbumin was replaced by bovine serum albumin in the incubation mixture (not shown). The LMW forms were never present in the carnosine samples. A good measure for the effectiveness of an

TABLE 5

OVALBUMIN
Percent Area of Chromatogram

|  | HMW | Monomer | LMW |
| --- | --- | --- | --- |
| t₀ hours |  |  |  |
| Carnosine samples |  |  |  |
| [A] to [D] | 0 | 100 | 0 |
| [control] | 0 | 100 | 0 |
| Aminoguanidine samples |  |  |  |
| [A] to [D] | 0 | 100 | 0 |
| [control] | 0 | 100 | 0 |
| after 7 hours |  |  |  |
| Carnosine samples |  |  |  |
| [A] | 9 | 91 | 0 |
| [B] | 6 | 94 | 0 |
| [C] | 3 | 97 | 0 |
| [D] | 25 | 75 | 0 |
| [control] | 68 | 32 | 0 |
| Aminoguanidine samples |  |  |  |
| [A] | 0 | 31 | 69 |
| [B] | 8 | 20 | 72 |
| [C] | 0 | 41 | 49 |
| [D] | 38 | 40 | 22 |
| [control] | 68 | 32 | 0 |

Legend: ovalbumin was incubated with DHA for 7 hours in the presence of various concentrations of either carnosine or aminoguanidine. Reaction products were separated on a gelfiltration column (Superose 6) and peaks grouped according to their retention times: HMW, high molecular weight (15–30 min); albumin monomer (35 min); and late eluting compounds LMW, low molecular weight (>40 min). Carnosine and aminoguanidine concentration [control] 0 mM, [A] 600 mM, [B] 300 mn, [C] 100 mM, [D] 50 mM.

anti-glycator is the amount of unmodified ovalbumin remaining after 7 hours of reaction. Here carnosine was more effective at all concentrations compared to aminoguanidine.

EXAMPLE 7

The Effect of Carnosine on Atherosclerosis

Figure 2:
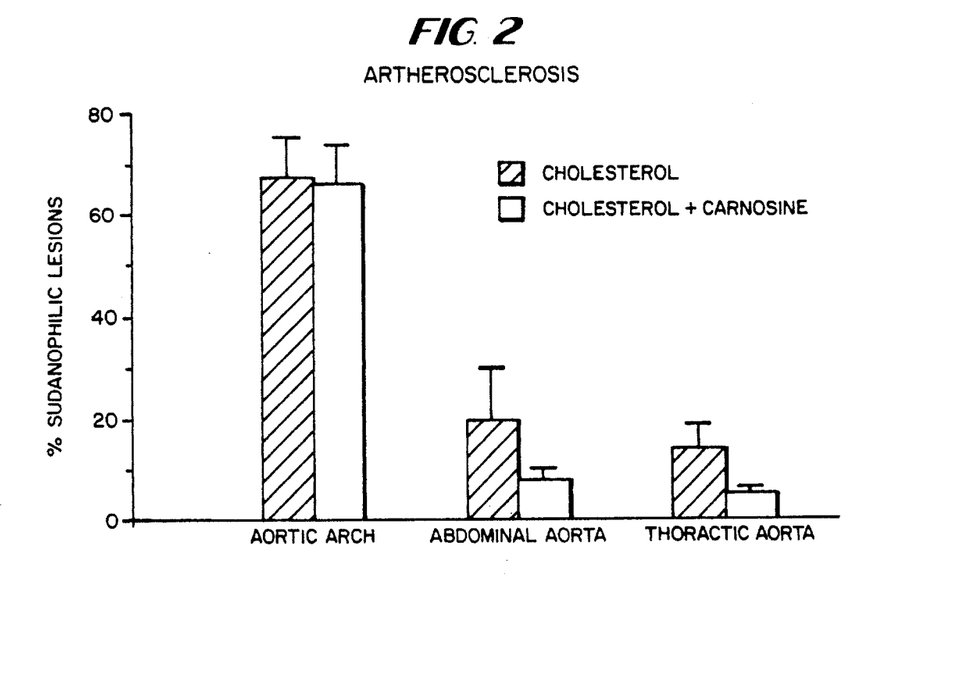
FIG. 2 shows the effect of carnosine on atherosclerosis (■ cholesterol, □ cholesterol plus carnosine)

Coronary heart disease is one of the most common causes of deaths in diabetics and non-diabetics alike. Glycation has been implicated in the development of atherosclerotic plaques in addition to many diabetic complications including diabetic kidney and eye disease. Cholesterol-fed rabbits were used to examine the effect of carnosine on atherosclerotic plaques formation over a period of 8 weeks. Our studies have shown that inhibition of glycation with carnosine can reduce but not prevent plaque formation. These results are shown in FIG. 2.

The two tailed P values for the data were calculated using the Mann-Whitney two sample test: thoracic aorta=0.0529; abdominal aorta= 0.5368; aortic arch= 0.6623, all data carnosine (n=6) feeding versus diabetic control (n=5). For comparison aminoguanidine gave the following results in a similar experiment: thoracic aorta=0.12; abdominal aorta= 0.044; aortic arch= 0.067, all data aminoguanidine (n=11) feeding versus diabetic control (n=12). More animals were used in this study giving a statistically better result. However, there are clear indications that both inhibitors of non-enzymatic glycosylation can reduce plaque formation.

The body weight of the animals reduced over the 8 week treatment period, however there was no difference between the control and carnosine treated group. No difference in weight of various organs was observed in control versus carnosine treatment.

|  | Body Weight in kg | |
|---|---|---|
|  | Week 0 | Week 8 |
| Control | 3.27 ± 0.09 | 2.75 ± 0.17 |
| Carnosine | 3.33 ± 0.09 | 2.68 + 0.12 |

| Weight of organs (g) after 8 weeks treatment | | |
|---|---|---|
|  | Liver | Kidney | Heart |
| Control | 135.94 ± 5.06 | 16.20 ± 0.67 | 7.92 ± 0.53 |
| Carnosine | 124.40 ± 6.36 | 17.53 ± 0.69 | 6.12 ± 0.27 |

EXAMPLE 8

The Effect of Carnosine on the Formation of Cataracts in Diabetic Rats

Cataract is an opacification of the ocular lens sufficient to impair vision. Diabetes has been associated with cataract for many years and many laboratory experiments support the view that diabetes is the cause of one form of cataract. Diabetes in animals can be induced by streptozotozin and opacity of the lens starts to develop by 20 days after injection but dense opacities appear only after about 100 days depending on age at injection.

Figure 3:
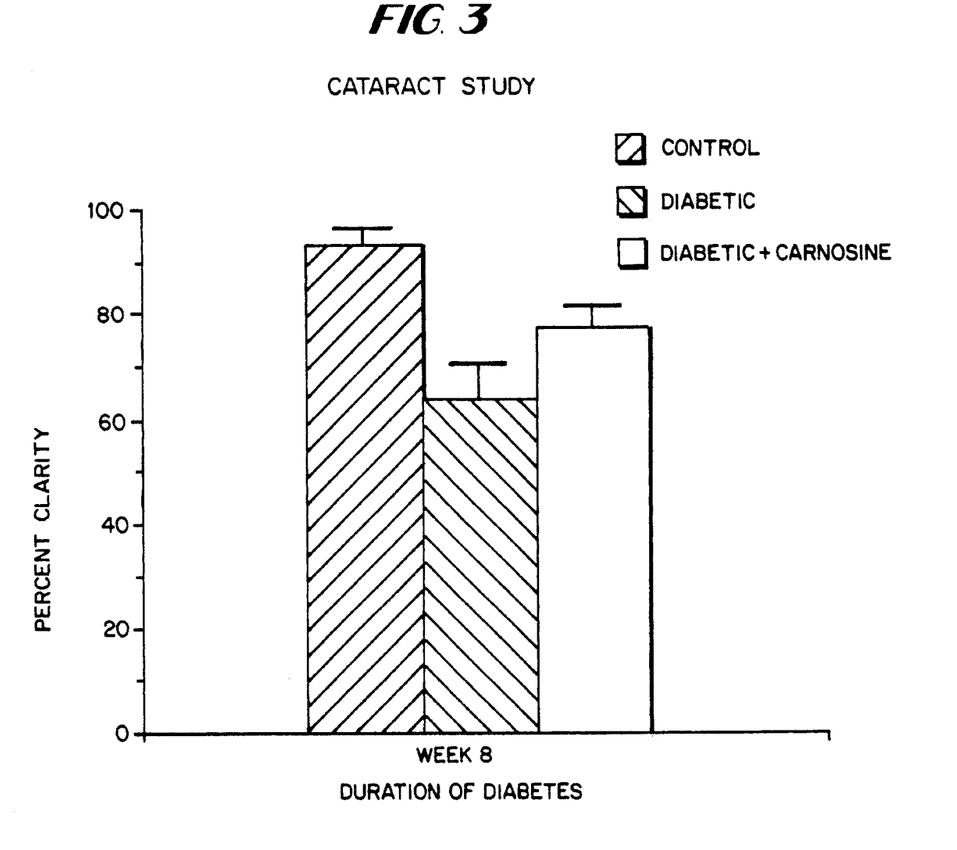
FIG. 3 shows the effect of carnosine on formation of cateracts in diabetic rats (▲control, ■diabetic □ diabetic plus camosine).

In cataract adducts of sugars to proteins including lens proteins have been identified and quantified. In most tissues there is little accumulation of late Maillard products even in diabetes but proteins in the lens nucleus have time not only to accumulate early glycation products but also for them to change into yellow Maillard products. The initial attack of a sugar leads to a variety of chemical entities and induces structural changes to enzymes, membrane proteins and crystallins in the lens and therefore several pathways can lead to damage. A compound like carnosine with its ability to scavenge the reaction aldehyde group of sugars should reduce the onset of cataract. We have tested this in the streptozotocin induced diabetic rat model. After 8 week on a carnosine diet the animals showed a higher clarity (less opacity) compared to a diabetic control group (Mann Whitney two sample test, two tailed p value=0.2092; carnosine feeding versus diabetic control) (see FIG. 3). Since this was measured at 56 days, the half way mark of the experiment, the trend indicates a reduction in cataract formation by carnosine feeding.

Cataract can not only be induced by reducing sugars in animal models. Babizhayev (1989) has shown that lipid peroxidation can be one initiatory cause of cataract development in animal models. Injection of a suspension of liposomes prepared from phospholipids containing lipid peroxidation products induces the development of posterior subcapsular cataract. According to his finding such modelling of cataract is based solely on lipid peroxidation and can be inhibited by antioxidants like carnosine. The formation of Maillard reaction products however, is an independent pathway and cannot be influenced by antioxidants.

EXAMPLE 9

The Effect of Carnosine on Proteinuria, Glycated Haemoglobin and Blood Glucose Levels in Diabetic Rats At week 8 no significant changes were observed for the following parameters:

| normal | diabetic | diabetic + carnosine |
|---|---|---|
| Albuminuria | | |
| 2.4 x/÷ 1.3 | 2.51 x/÷ 1.07 | 2.51 x/÷ 1.48 |
| Percent Glycated Haemoglobin (HbAl$_c$) | | |
| 1.5 ± 0.1 | 4.83 ± 0.23 | 4.49 ± 0.14 |
| Blood Glucose (mM mean + SEM) | | |
| 10.0 ± 1.5 | 29.84 ± 4.88 | 22.63 ± 3.00 |

Changes in proteinuria and retinopathy can only be observed after about 30 weeks of diabetic condition. The compound aminoguanidine, usually used for the prevention of non-enzymatic glycosylation does not reduce the amount of glycated haemoglobin in diabetic models even after 30 weeks of feeding. This study is presently continuing.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Literature:

Gulewitsch, W., & Amiradzibi, S. (1900) Ber. Dtsch. Chem. Ges. 33, 1902–1903

Maillard, L. C. (1912) C.R. Acad. Sci. 154, 66–68

Shilton, B. H., & Walton, D. J. (1991) J. Biol. Chem. 266, 5587–5592

Hammes, H. P., Martin, S., Federlin, K., Brownlee (1991) Proc. Natl. Acad. Sci USA 88, 11555–11558

Kim, S. B., Kim, I. S., Yeum, D. M., & Park, Y. H. (1991) Mut. Res. 254, 65–59

Maron, D. M. and Ames, B. N. (1983) Mut. Res. 113, 173–215

Babizhayev, M. A. (1989) Biochimica et Biophysica Acta 1004, 363–371

We claim:

1. A method for the treatment of the complications and pathology of diabetes in a diabetic subject comprising administering to the subject a composition comprising a compound selected from the group consisting of (β-Ala-His)$_n$, (Lys-His)$_n$, a compound of the formula $R_1$-X-$R_2$, pharmaceutically acceptable salts thereof and combinations thereof; and a pharmaceutically acceptable carrier, in which n is 2-5, $R_1$ is one or two naturally occurring amino acids, $R_2$ is 1 or 2 naturally amino acids, and X is $R_3$-(L or D-His)($R_4$)-$R_5$ where $R_3$ is void or ω-aminoacyl with 1 to 12 carbon atoms, $R_4$ is void or imidazole modification with alkyl-sulphydryl, hydroxyl, halogen and/or amino groups, and $R_5$ is void or carbonxyl (alkyl) amides with 1 to 12 carbon atoms.

2. A method as claimed in claim 1 in which the compound is selected from the group consisting of carnosine, anserine, ophidine, homocarnosine, homoanserine, D-carnosine and carcinine.

3. A method as claimed in claim 2 in which the compound is carnosine.

4. A method as claimed in claim 1 in which $R_1$ and $R_2$ are L- or D-lysine or L- or D-aspartic acid or L- or D-glutamic acid or homologues thereof.

5. A method as claimed in claim 1 in which the composition further comprises aminoguanidine.

6. A method as claimed in claim 1 in which the composition is co-administered with insulin sulfonylureas, biguanides and/or amylin blockers.

7. A method as claimed in claim 1 in which the composition is administered by injection, infusion, ingestion, inhalation, opthalmically, iontophoresis or topical application.

8. A method as claimed in claim 1 in which the composition is administered orally or opthalmically.

9. A method as claimed in claim 1 in which the compound is mixed with another molecule which molecule is such that the composition is improved in regard to skin penetration, skin application, tissue absorption/adsorption, skin sensitisation and/or skin irritation.

10. A method as claimed in claim 9 in which the molecule is selected from the group consisting of sodium lauryl sulphate, lauryl ammonium oxide, ozone, decylmethylsulphoxide, lauryl ethoxylate, octenol, dimethylsulphoxide, propyleneglycol, nitroglycerine, ethanol and combinations thereof.

11. A method a claimed in claim 1, wherein said one or two naturally occurring amino acids are alpha-amino acetylated with alkyl or aralkyl of 1 to 12 carbon atoms.

12. A method as claimed in claim 11, wherein said alkyl or aralkyl groups contain 2 to 6 carbon atoms.

13. A method as claimed in claim 11, wherein said naturally occurring amino acids in the definition of $R_2$ are alpha-carboxyl esterified or amidated with alkyl or aralkyl of 1 to 12 carbon atoms.

14. A method as claimed in claim 13, wherein said alkyl or aralkyl groups of 2 to 6 carbon atoms.

15. A method as claimed in claim 1, wherein said ω-aminoacyl group contains 2 to 6 carbon atoms.

16. A method as claimed in claim 1, wherein said carbonxyl (alkyl) amides in $R_5$ contain 2 to 6 carbon atoms.

* * * * *